(12) United States Patent
Urban et al.

(10) Patent No.: US 12,113,722 B2
(45) Date of Patent: Oct. 8, 2024

(54) DATA TRANSMISSION DEVICE, MEDICAL IMAGING DEVICE AND METHOD FOR TRANSMITTING DATA PACKETS

(71) Applicant: Siemens Healthcare AG, Forchheim (DE)

(72) Inventors: Andreas Urban, Bayern (DE); Jutta Kiesel, Forchheim (DE); Harald Karl, Fuerth (DE); Bing Liu, Shanghai (CN)

(73) Assignee: Siemens Healthineers AG, Forchheim (DE)

( * ) Notice: Subject to any disclaimer, the term of this patent is extended or adjusted under 35 U.S.C. 154(b) by 148 days.

(21) Appl. No.: 17/845,217

(22) Filed: Jun. 21, 2022

(65) Prior Publication Data
US 2022/0417185 A1    Dec. 29, 2022

(30) Foreign Application Priority Data
Jun. 23, 2021   (DE) .......................... 10 2021 206 498

(51) Int. Cl.
*H04L 49/9057*   (2022.01)
*H04L 67/12*   (2022.01)

(52) U.S. Cl.
CPC .......... *H04L 49/9057* (2013.01); *H04L 67/12* (2013.01)

(58) Field of Classification Search
CPC ... H04L 47/56; H04L 49/9057; H04L 1/0002; H04L 47/625; H04L 49/3027; H04L 67/12; A61B 6/032; A61B 6/035; A61B 6/56
See application file for complete search history.

(56) References Cited

U.S. PATENT DOCUMENTS

| | | | |
|---|---|---|---|
| 8,797,877 B1 * | 8/2014 | Perla | H04L 49/90 370/252 |
| 11,005,778 B1 * | 5/2021 | Yonai | H04L 47/6255 |
| 11,240,151 B2 * | 2/2022 | Frink | H04L 45/586 |
| 2013/0195249 A1 | 8/2013 | Edler et al. | |
| 2014/0313996 A1 | 10/2014 | Suga | |

(Continued)

FOREIGN PATENT DOCUMENTS

| | | |
|---|---|---|
| CN | 105474589 A | 4/2016 |
| CN | 105474590 A | 4/2016 |

(Continued)

*Primary Examiner* — Mounir Moutaouakil
(74) *Attorney, Agent, or Firm* — Harness, Dickey & Pierce, P.L.C.

(57) ABSTRACT

In an example embodiment a data transmission device for transmitting data packets comprises at least one receive interface configured to receive data packets from a respective data source; a respective receive buffer configured to buffer the data packets received via the respective receive interface; a transfer device configured to transfer the data packets from the respective receive buffer to a transmit buffer, the transmit buffer selected for the respective data packet from a plurality of existing transmit buffers; and a respective transmit interface configured to transmit the data packets stored in the respective transmit buffer to a receiving device, wherein the transfer device is configured to transfer the respective data packet from the respective receive buffer into the selected transmit buffer only when an enable condition exists, the enable condition being based on a fill level of one of the transmit buffers other than the selected transmit buffer.

15 Claims, 4 Drawing Sheets

(56) References Cited

U.S. PATENT DOCUMENTS

| | | |
|---|---|---|
| 2016/0157268 A1 | 6/2016 | Wakabayashi et al. |
| 2016/0191424 A1* | 6/2016 | Srinivasan .......... H04L 49/3045 370/359 |
| 2016/0205025 A1 | 7/2016 | Wakabayashi et al. |
| 2016/0226797 A1* | 8/2016 | Aravinthan ........... H04L 49/252 |
| 2017/0034843 A1 | 2/2017 | Liu et al. |
| 2019/0334828 A1* | 10/2019 | Fairhurst ............... H04L 49/103 |
| 2019/0334837 A1 | 10/2019 | Fairhurst et al. |
| 2020/0204398 A1 | 6/2020 | Jerolm et al. |

FOREIGN PATENT DOCUMENTS

| | | | |
|---|---|---|---|
| CN | 111052682 A | 4/2020 | |
| CN | 112765054 A | 5/2021 | |
| DE | 102012201222 A1 | 6/2013 | |
| DE | 102012217597 B4 * | 9/2014 | .............. A61B 6/56 |
| EP | 2797269 A1 | 10/2014 | |

* cited by examiner

DATA TRANSMISSION DEVICE, MEDICAL IMAGING DEVICE AND METHOD FOR TRANSMITTING DATA PACKETS

CROSS-REFERENCE TO RELATED APPLICATION(S)

The present application claims priority under 35 U.S.C. § 119 to German Patent Application No. 102021206498.1, filed Jun. 23, 2021, the entire contents of which are incorporated herein by reference.

FIELD

Some example embodiments of the present invention relate to a data transmission device for transmitting data packets, such as measurement data of a medical imaging device. In addition, some example embodiments of the present invention relate to a medical imaging device and a method for transmitting data packets.

BACKGROUND

In the field of medical imaging, e.g. in computed tomography (CT), and also in other fields of application, it may be necessary to transmit data between components that move relative to one another. For example, the imaging X-ray sensors in CT scanners are typically disposed on a gantry that is rotatably mounted with respect to a base, and data processing or visualization is to be performed by components that are fixed with respect to the base, e.g. workstation computers or fixed image processors. In modern CT scanners, for example, very high data rates of e.g. 35 Gbit/s may be used, which places exacting requirements on such a communication link.

In principle, such data transmission can take place via sliding contacts, for example. However, in order to achieve high data rates with low maintenance and low susceptibility to interference, it may be advantageous to use wireless data transmission over short distances instead. For example, data can be transmitted by radio or generally by RF technology or via capacitive coupling.

Here it is advantageous for several reasons to provide a plurality of simultaneously usable radio channels. On the one hand, the data transmission rate can be increased. On the other hand, e.g. due to the rotation of a gantry, transmit antennas used are moved past receive antennas used, so that, for example, individual transmit antennas may be temporarily located in areas where their signals cannot be reliably received by receive antennas. It is therefore advantageous to use a plurality of transmit and receive antennas so that, for example, communication is always possible via at least one or at least a certain number of channels regardless of the angle of rotation of a gantry.

Since hybrid transmission systems, in which part of the transmission path is wired and part of the transmission path is wireless, typically achieve different transmission rates in the different parts of the transmission path, "store and forward" techniques, i.e. in particular FIFO (first in, first out) buffering of data packets, are typically used in the transition region between wired and wireless transmission, and vice versa. As will be explained later with reference to FIG. 2, the combination of employing a plurality of transmission channels and the buffering used can in some cases result in the sequence of transmitted data packets being changed.

In principle, this could be acceptable, for example, if a data packet processing device, such as a workstation computer used to generate the three-dimensional image data in the context of a CT scan, first stores the received packets and puts them in the correct order before further processing takes place.

SUMMARY

However, since very high data rates are used in a CT scan, such a subsequent re-ordering of received data packets would result in considerable additional requirements in terms of the computing time required and the speed and amount of available memory, especially if measurement data is to be visualized in near real time. For example, near-real-time data visualization would therefore only be feasible with considerable limitations, at least for devices in the lower price segment.

Some example embodiments of the present invention provide an improved means of achieving a correct packet sequence even when data buffering is combined with a plurality of transmission channels.

At least one example embodiment provides a data transmission device for transmitting data packets comprising at least one receive interface configured to receive data packets from a respective data source; a respective receive buffer configured to buffer the data packets received via the respective receive interface; a transfer device configured to transfer the data packets from the respective receive buffer to a transmit buffer, the transmit buffer selected for the respective data packet from a plurality of existing transmit buffers; and a respective transmit interface configured to transmit the data packets stored in the respective transmit buffer to a receiving device, wherein the transfer device is configured to transfer the respective data packet from the respective receive buffer into the selected transmit buffer only when an enable condition exists, the enable condition being based on a fill level of one of the transmit buffers other than the selected transmit buffer.

According to at least one example embodiment, for evaluating the enable condition, the transfer device is configured to consider, as another transmit buffer, the transmit buffer into which another data packet has been transferred which was received immediately prior to the data packet to be transferred into the selected transmit buffer.

According to at least one example embodiment, for evaluating the enable condition, the transfer device is configured to consider, as another transmit buffer, the transmit buffer into which another data packet has been transferred which was received via the same receive interface immediately before the data packet to be transferred to the selected transmit buffer.

According to at least one example embodiment, the enable condition is based on the length of the data packet to be transferred to the selected transmit buffer.

According to at least one example embodiment, the fill level indicates a length of a remaining partial data packet or another data packet previously transferred into the other transmit buffer, the partial data packet has not yet been transmitted via the transmit interface assigned to the other transmit buffer, wherein the enable condition exists if the length of the data packet to be transferred to the selected transmit buffer attains or exceeds the length of the partial data packet or the sum of the length of the partial data packet and a predetermined offset value.

According to at least one example embodiment, at least one of, the receive interface is connected or connectable by wire to the respective data source, or the respective transmit interface is configured for wireless transmission of the respective data packet to the receiving device.

According to at least one example embodiment, the data transmission device is configured to transmit measurement data of a medical imaging device as data packets.

At least one example embodiment provides a medical imaging device comprising the data transmission device of at least one example embodiment.

According to at least one example embodiment, the medical imaging device further includes a sensor device, wherein the sensor device is configured to supply data packets to the data transmission device as the data source or via a processing device used as the data source.

According to at least one example embodiment, the medical imaging device further includes a framework movably mounted with respect to a base, the framework incorporating the data source and the data transmission device, wherein the receiving device is fixed relative to the base.

According to at least one example embodiment, the medical imaging device is a CT scanner or comprises a CT scanner, the sensor device is an X-ray sensor or comprises an X-ray sensor, or the movably mounted framework is a rotatable gantry.

At least one example embodiment provides a method for transmitting data packets comprising receiving data packets from a respective data source; temporarily storing the received data packets in a receive buffer; transferring the data packets from the receive buffer into a transmit buffer selected for the respective data packet from a plurality of existing transmit buffers, wherein the respective data packet is only transferred from the respective receive buffer into the selected transmit buffer if an enable condition exists, the enable condition being based on a fill level of one of the transmit buffers other than the selected transmit buffer; and transmitting the data packets stored in the respective transmit buffer to a receiving device by a respective transmit interface assigned to the transmit buffer.

According to at least one example embodiment, at least one of measurement data of a medical imaging device is transmitted as data packets, data packets are received from the respective data source via a wired connection, or the data packets stored in the respective transmit buffer are transmitted to the receiving device via a wireless connection by the respective transmit interface assigned to the transmit buffer.

At least one example embodiment provides a non-transitory computer readable medium, comprising instructions, during the execution of which data packets are transferred by a transfer device from a receive buffer to a transmit buffer selected for the respective data packet from a plurality of existing transmit buffers wherein transfer of the respective data packet from the respective receive buffer into the selected transmit buffer takes place only if an enable condition exists, the enable condition being based on a fill level of one of the transmit buffers other than the selected transmit buffer.

BRIEF DESCRIPTION OF THE DRAWINGS

Further advantages and details example embodiments of the present invention will emerge from the following exemplary embodiments and the accompanying schematic drawings in which.

DETAILED DESCRIPTION

Some example embodiments according to the present provide a data transmission device, wherein the transfer device is designed to transfer the respective data packet from the respective receive buffer into the selected transmit buffer only when an enable condition is fulfilled, the fulfillment of which depends on a fill level of a transmit buffer other than the transmit buffer selected.

The inventive delaying of the transfer of the data packet into the selected transmit buffer until the enable condition is fulfilled makes it immediately possible, by introducing a suitable delay, to prevent the packet sequence from being changed due to parallel data transmission via the transmit interfaces assigned to the different transmit buffers, so that the packets are reliably received in the correct sequence by the receiving device and thus no subsequent correction of the packet sequence is required. This enables the received data packets to be further processed with considerably less technical overhead. At the same time, it has been recognized that the delaying of individual data packets if the enable condition is not fulfilled only insignificantly reduces the achievable data rate in real applications and also barely increases latencies resulting from the data transmission. Thus, for example, the advantages of parallel wireless data transmission can be exploited without the need for complex post-processing of the data to correct the packet sequence.

In particular, the transfer device can transfer the oldest data packet in each case, e.g. the oldest information, from the receive buffer to the selected transmit buffer. The receive buffer can thus implement a FIFO buffer (first in, first out). The transmit buffer can also serve as a FIFO buffer for the transmit interface, i.e. the transmit interface can first read, from the transmit buffer, the earliest data written thereto.

The selected transmit buffer can be selected based on the operational status of the data transmission device or of a larger device in which it is incorporated, such as a medical imaging device. For example, as explained above, it may be the case that certain transmit interfaces are temporarily unable to transmit data packets to the receiving device, e.g. due to the current position of their transmit antennas. It may therefore be advisable to select the transmit interface used, and thus the transmit buffer, according to a rotational position of a gantry. In addition, in order to achieve optimum utilization of the available transmission channels and thus of the available bandwidth, an empty transmit buffer or one that is as empty as possible can be selected.

For evaluating the enable condition, the transfer device can be designed to consider, as another transmit buffer, the transmit buffer into which another data packet was transmitted that was received immediately prior to the data packet to be transmitted to the selected transmit buffer.

In particular, as part of evaluating the enable condition, the transfer device can be designed to consider, as another transmit buffer, the transmit buffer into which another data packet was transmitted that was received via the same receive interface immediately prior to the data packet to be transmitted to the selected transmit buffer.

In most scenarios, particularly if the data transmission rates in respect of reception by the receive interface and transmission by the transmit interface are not overly different, it is already inherent in the system, regardless of the checking of the enable condition, that transmission of the penultimate data packet will have been completed before the current data packet is transmitted. It is therefore usually sufficient to ensure, in terms of the enable condition, that transmission of the immediately preceding data packet to the receiving device or further devices downstream of the receiving device, e.g. a processing device, is completed before the current data packet is transmitted to it.

The fulfillment of the enable condition can additionally depend on the length of the data packet to be transferred to the selected transmit buffer. The length of the data packet can be specified e.g. in bytes or, more generally, in characters. It is possible for the length of the data packet to be determined when it is received or rather when it is written to the receive buffer. For many common communication protocols, the data packets themselves include information about their length, e.g. in a header. The length of the data packet can also be determined on the basis of specific start and end markers.

As will be explained in more detail below, a delay to ensure correct packet order can be relevant particularly for relatively short data packets, which is why it is advantageous to take the length into account.

The fill level can describe a length of a remaining partial data packet of the or another data packet previously transmitted to the other transmit buffer, which partial data packet has not yet been transmitted via the transmit interface assigned to the other transmit buffer, wherein the enable condition is fulfilled or can only be fulfilled if the length of the data packet to be transmitted to the selected transmit buffer reaches or exceeds the length of the partial data packet or the sum of the length of the partial data packet and a predetermined offset value.

An undesirable change in the packet sequence would result if the transmission of a data packet sent later to the receiving device or to a device downstream of the receiving device were to be completed before the transmission of an earlier data packet sent there has been completed, since data packets are usually forwarded or further processed only after they have been completely received. As a rule, especially if the data packets are transmitted wirelessly from the transmit interface to the receiving device, transmission from the transmit buffer to the receiving device or to said downstream device results in lower transmission speeds than those achieved for transfer from the receive buffer to the transmit buffer. If the length of the remaining partial data packet is thus greater than the length of the partial data packet to be transferred to the transmit buffer, this can result in the time required for complete transmission of the partial data packet to the receiving device or to a device downstream of this device exceeding the sum of the relatively short time required for transmission of the data packet in the transmit buffer and the time required for transmission of this data packet from the transmit buffer to the receiving device or to the downstream device, which would result in a change in the sequence of the data packets. This can be avoided by the described procedure.

In many applications, transmission rates or rather transit times for the transmission path from the transmit buffer to the receiving device or to downstream devices can vary to a certain extent. For example, the required transmission time for wireless transmission can depend on the relative position of the transmitter and receiver, which may change e.g. in the case of transmission from a moving gantry to a stationary base depending on the rotational position of the gantry. In addition, transmission interference can cause this time to vary. Even in the case of wired transmission, slight transmission time variations may result, e.g. due to a plurality of possible transmission paths and/or temporary buffering as part of the transmission.

The variable transmission time can mean that even in cases where the data packet to be transmitted to the transmit buffer is slightly longer than the remaining partial data packet, this data packet is fully received by the receiving device or a downstream device before the remaining partial data packet is fully received, i.e. the order of the data packets changes. This problem can be compensated by using the predefined offset. A suitable offset can, for example, already be estimated as part of system design or determined by test measurements and then fixed.

The length of the remaining partial data packet is usually known anyway, since, on the one hand, the length of the data packet and, on the other hand, the amount of data already transmitted from it are known. Alternatively, it would be possible to determine the length of the partial data packet or also of a data packet placed in a buffer, e.g. by determining a distance between a read pointer and a write pointer on the corresponding buffer, or more complex data structures can be used in which entries to a data structure are counted, e.g. as part of object orientation.

The respective receive interface can be wired or wirable to the respective data source. Additionally or alternatively, the respective transmit interface can be designed for wireless transmission of the respective data packet to the receiving device. Thus, in particular, a hybrid transmission path can be used in which wired transmission of the data packets takes place in sections of the transmission path and wireless transmission of the data packets takes place in other sections of the transmission path. Nevertheless, as explained above, it can be ensured that the data packets arrive at the receiver in the correct order.

As already explained, the data transmission device can be used in particular for transmitting measurement data of a medical imaging device as data packets.

In addition to the data transmission device according to example embodiments of the present invention, example embodiments of the present invention relates to a medical imaging device, in particular a CT scanner, wherein the imaging device comprises a data transmission device according to. As detailed above, the data transmission device according to example embodiments of the present invention can be particularly advantageous where data is to be transmitted at relatively high data rates between components moving relative to one another, as is the case e.g. in CT scanners and other medical imaging devices.

The imaging device can comprise a sensor device, which is in particular an X-ray sensor or comprises an X-ray sensor, wherein the sensor device is designed to supply data packets to the data transmission device as the data source or via a processing means used as the data source. In particular, the sensor device can provide image data, such as X-ray images.

The medical imaging device can comprise a framework movably mounted with respect to a base, in particular a rotatably mounted gantry, comprising the data source and the data transmission device, wherein the receiving device is fixed relative to the base. Here, the data transmission device can be used in particular to transmit from a moving coordinate system, e.g. a rotating gantry, to a stationary coordinate system. If short-range wireless transmission is used, depending on the movement position or rotation angle of the gantry with respect to the base, in each case only parts of the transmit interfaces or of the transmit antennas assigned to them can be disposed in such a way that their signal can be reliably received by a respective receive antenna of the receiving device. This can be taken into account for selecting the transmit buffer into which a data packet is transmitted, and thus for the transmit interface to be used.

As mentioned above, the imaging device can be or comprise a CT scanner, and/or the sensing device can be or comprise an X-ray sensor, and/or the movably mounted framework can be a rotatably mounted gantry.

At least one example embodiment of the present invention further relates to a method for transmitting data packets, wherein.

data packets are received from a respective data source and temporarily stored in a receive buffer, the data packets are transferred from the receive buffer to a transmit buffer selected for the respective data packet from a plurality of existing transmit buffers, wherein transfer of the respective data packet from the respective receive buffer to the selected transmit buffer takes place only if an enable condition is fulfilled, the fulfillment of which depends on a fill level of a transmit buffer other than the selected transmit buffer, and the data packets stored in the respective transmit buffer are transmitted to a receiving device by a respective transmit interface assigned to the transmit buffer.

In particular, measurement data of a medical imaging device can be transmitted as data packets in this process. In addition or alternatively, the data packets can be received from the respective data source via a wired connection. Additionally or alternatively, the data packets stored in the respective transmit buffer can be transmitted to the receiving device by the respective transmit interface associated with the transmit buffer via a wireless connection.

In particular, the method according to at least one example embodiment of the present invention can be implemented by the data transmission device according to at least one example embodiment of the present invention or can be used in the medical imaging device according to at least one example embodiment of the present invention for data transmission. In particular, the data transmission device according to at least one example embodiment of the present invention can be designed to carry out the method according to at least one example embodiment of the present invention. Irrespective thereof, the features explained in connection with the data transmission device according to at least one example embodiment of the present invention or for the medical imaging device according to at least one example embodiment of the present invention, including the advantages detailed there, are applicable to the method according to at least one example embodiment of the present invention, and vice versa.

In particular, in the context of evaluating the enable condition, the transmit buffer that can be considered as the other transmit buffer is the one to which another data packet received immediately prior to the data packet to be transferred to the selected transmit buffer has been transmitted. In addition or alternatively, fulfillment of the enable condition can additionally depend on the length of the data packet to be transmitted to the selected transmit buffer. For further embodiments in this respect, reference is made to the above explanations of the data transmission device according to at least one example embodiment of the present invention.

At least one example embodiment of the present invention also relates to a computer program comprising instructions, during the execution of which data packets are transferred by a transfer device from a receive buffer to a transmit buffer selected for the respective data packet from a plurality of existing transmit buffers, wherein the transfer of the respective data packet from the respective receive buffer into the selected transmit buffer takes place only if an enable condition is fulfilled, the fulfillment of which depends on a fill level of a transmit buffer other than the selected transmit buffer. The transfer device can be any programmable processing device which has at least read access to a receive buffer or to a memory area constituting it and at least write access to a plurality of transmit buffers or to respective memory areas constituting the transmit buffers. A CPU, a microcontroller or an FPGA, for example, can be used as such a processing device or transfer device.

The instructions of the computer program can in particular implement the part of the method according to at least one example embodiment of the present invention in which the data packets are transferred from the receive buffer to the selected transmit buffer and in which the enable condition is checked. Features explained above with respect to the method according to at least one example embodiment of the present invention are thus applicable accordingly to the computer program according to at least one example embodiment of the present invention.

The transfer device programmed by the computer program according to at least one example embodiment of the present invention can be used as a transfer device in the data transmission device according to at least one example embodiment of the present invention or the imaging device according to at least one example embodiment of the present invention. Features disclosed with respect to these items are therefore applicable to the computer program according to at least one example embodiment of the present invention together with the advantages cited.

At least one example embodiment of the present invention also relates to a computer-readable data carrier comprising a computer program according to at least one example embodiment of the present invention.

The described functionality or the transfer device used in the data transmission device according to at least one example embodiment of the present invention can also be implemented by hardwiring a corresponding functionality, e.g. by an ASIC, instead of by a computer program.

Figure 1:
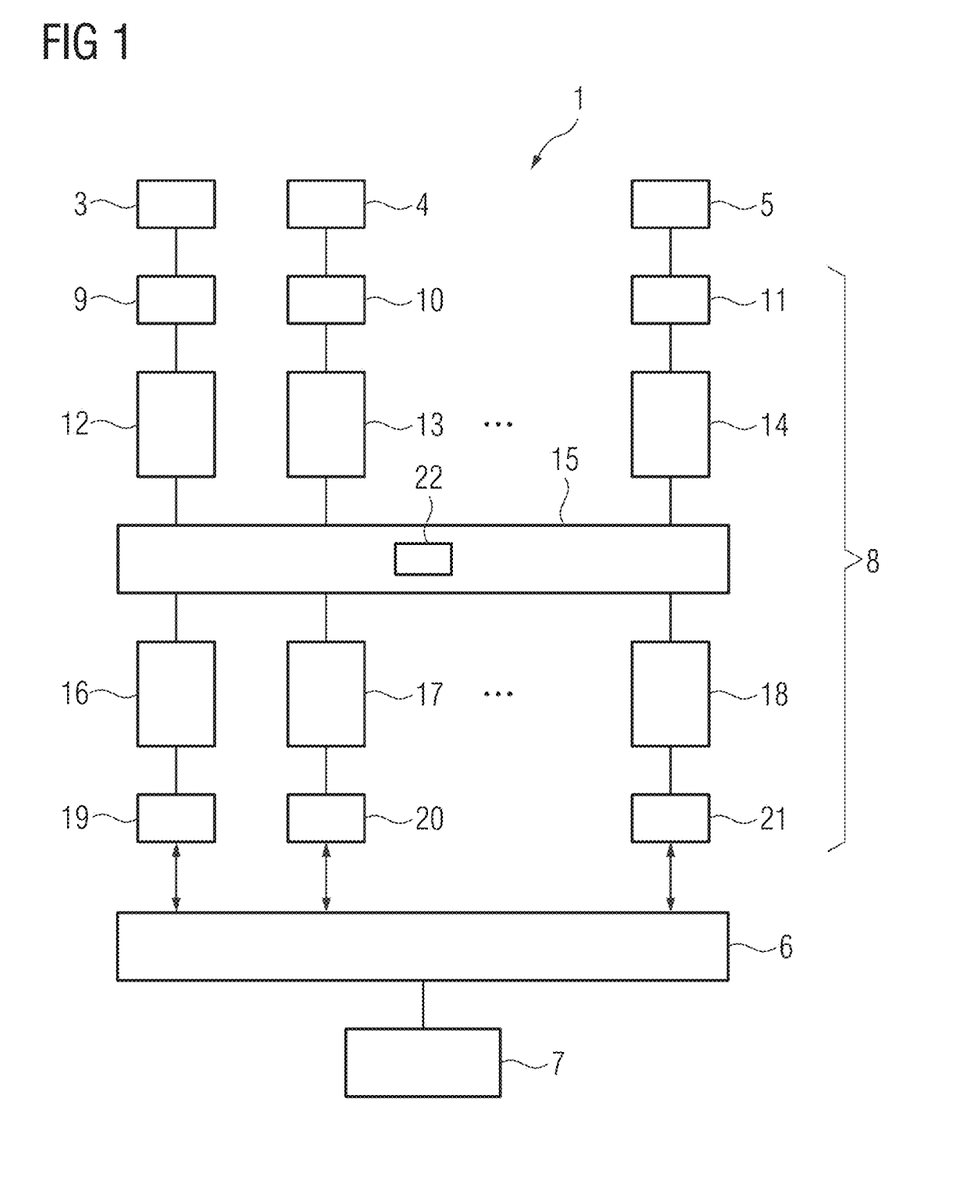
FIG. 1 shows an exemplary embodiment of a medical imaging device according to example embodiments of the present invention, comprising an exemplary embodiment of the data transmission device, wherein an exemplary embodiment of the method is used to transmit the data packets.

FIG. 1 schematically illustrates components of a medical imaging device that are relevant to the provision, transmission and processing of measurement data. A specific embodiment of a corresponding medical imaging device as a CT scanner will be explained in more detail below with reference to FIG. 4.

The imaging device 1 comprises a plurality of data sources 3, 4, 5, which are constituted in particular by sensor devices, e.g. by an X-ray sensor of a CT scanner. Alternatively, the data sources 3, 4, 5 can also be constituted, at least in part, by processing devices that already perform preprocessing of measurement data provided by sensors. The provided measurement data or rather data packets containing it are to be provided to a processing device 7 via a receiving device 6.

In the case of CT scanners, for example, it is common for the data sources to be moved relative to a base and thus typically also relative to the processing device 7 in the course of scanning, e.g. because they are disposed on a rotating gantry. The transition from the moving reference frame of the rotating gantry to the stationary reference frame of the base is made possible in the example by using a data transmission device 8 to which the data packets are transmitted by the data sources 3, 4, 5 in a wired manner and which can, for example, also be mounted on the gantry. Transmission from the data transmission device 8 to the receiving device 6, on the other hand, is wireless, so that the use of sliding contacts or the like for data transmission can be dispensed with.

The data transmission device 8 comprises a plurality of receive interfaces 9, 10, 11 via which data packets are received from data sources 3, 4, 5 respectively via cable. The received data packets are first stored in a respective receive buffer 12, 13, 14 and from there are stored by a transfer device 15 in a selected one of a plurality of transmit buffers 16, 17 18. Various transmit interfaces 19, 20, 21 transmit the data packets stored in one of the respective transmit buffers 16, 17, 18.

On the one hand, the use of a plurality of transmit interfaces 19, 20, 21 and associated transmit buffers 16, 17, 18 is advantageous if the transmit interfaces 19, 20, 21 cannot each be used at all times to transmit data packets during operation, i.e. not in every rotational position of a gantry, for example, because a transmit antenna used is not located in the range of a receive antenna of the receiving device 6. In addition, by distributing the received data packets over different transmit interfaces 19, 20, 21, parallelization of data transmission and thus a higher data throughput can be achieved.

In the example shown, received data packets are supplied by the receiving device 6 to only one other device, namely a processing device 7. However, it would also be possible to supply received data packets to a plurality of devices or to use address information in the data packets so that the receiving device 6 or a downstream device can distribute the data packets to various other devices depending on the content thereof.

To achieve minimum delays in data transmission and maximum data throughput, it would be ideal in principle if the transfer device 15 were to write data present in one of the receive buffers 12, 13, 14 directly and without delay to the transmit buffer 16, 17, 18 of the transmit interface 19, 20, 21 through which transmission of this data is to take place. However, due to the use of parallel transmission paths for wireless data transmission, different transmission rates achieved for wired and wireless data transmission, and the use of different data packet lengths, situations may occur using such an approach, however, whereby data packets are received by the receiving device 6 or the processing device 7, as the case may be, in a different order from that in which they were sent by the respective data source 3, 4, 5. An example of such a situation will be explained below with reference to FIG. 2.

In principle, it would be possible to correct an incorrect order of the received data packets by subsequently re-ordering them. However, since, for example, very high data rates of e.g. 35 Gbit/s are used in the field of computed tomography for transmitting the measurement results, subsequent re-ordering of the received packets is relatively complex in technical terms.

In the medical imaging device 1 or in the data transfer device 8, such disordering of the data packets at the receiving device 6 or the processing device 7 is therefore prevented as early as the data transfer stage. In order to make this possible, the transfer device 15 is designed to effect transfer of a respective data packet from the respective receive buffer 12, 13, 14 into the selected transmit buffer 16, 17, 18 only when an enable condition 22 is fulfilled, the fulfillment of which depends on a fill level of one of the transmit buffers 16, 17, 18 other than the selected transmit buffer 16, 17, 18. The effect and implementation of this enable condition 22 are explained in more detail below with reference to FIGS. 2 and 3.

Figure 2:
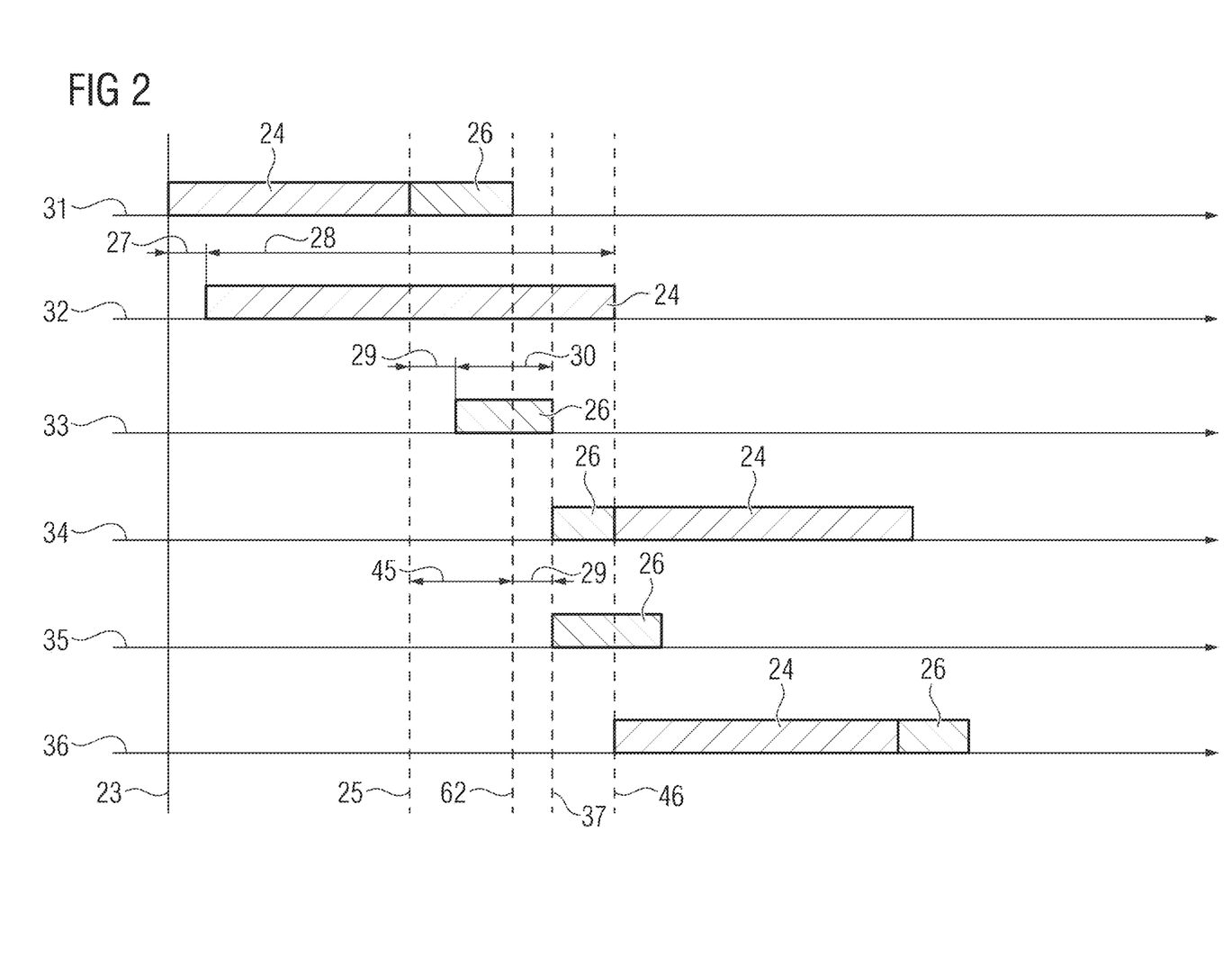
FIG. 2 shows the effect of evaluating the enable condition on the timing of the transmission of data packets in the medical imaging device shown in FIG. 1.

FIG. 2 shows, in a plurality of lines 31-36, the timing of different transmission processes in the medical imaging device 1. The transmission processes will first be explained for the case in which data stored in a receive buffer 12, 13, 14 is immediately transferred into a respective selected transmit buffer 16, 17, 18. This corresponds to the case in which the enable condition 22 would not be evaluated or would always be fulfilled.

Line 31 shows the transmission of two data packets 24, 26 from the data source 3 to the receive buffer 12. The first data packet 24 is received at time 23 and the second data packet 26 at time 25.

At time 23, the transfer device 15 detects that the transmit interface 19 is usable for transmitting, e.g. because a transmit antenna is in the receiving range of a receive antenna of the receiving device 6, and that the transmit buffer 16 is empty. The transmit buffer 16 is therefore selected to have the first data packet 24 copied thereto. As soon as parts of the data packet 24 enter the transmit buffer 16, the transmit interface 19 starts transmitting this data.

In FIG. 2, the time sequence of the reception of the first data packet 24 by the receiving device 6 is visualized in line 32. The start of reception is spaced from the time 23 by the time interval 27, since the copying of the data into the receive buffer 16 and in particular the wireless transmission to the receiving device 6 requires a certain amount of time. In addition, by comparing lines 31 and 32, it is readily apparent that a longer time interval 28 is required for reception of the data packet 24 by the receiving device 6 than the time interval between times 23 and 25, since a lower transmission rate is generally achieved for wireless transmission.

Since it is initially assumed that the enable condition 22 is not checked, the data of the second data packet 26 is also transferred into a selected transmit buffer 17 immediately after being stored in the receive buffer 12 and is transmitted from there, via the transmit interface 20, to the receiving device 6. The timing of reception of the second data packet 26 by the receiving device 6 for this case is visualized in line 33 of FIG. 2. As already explained above for the first data packet 24, reception of the second data packet 26 is also delayed by a short time interval 29 which is required for transferring the data from the receive buffer 12 to the transmit buffer 17 on the one hand and from the transmit buffer 17 to the receiving device 6 on the other hand. In addition, the time interval 30 for receiving the data packet 26 is extended relative to the duration shown in line 31 which is required for writing the data packet 26 to the receive buffer 12, since lower transmission rates are achieved for the wireless transmission than in the preceding wired transmission.

Transmission of the data packets 24, 26 from the receiving device 6 to the processing device 7 shall not take place until the respective packet 24, 26 has been completely received by the receiving device 6. Since higher transmission rates are typically achieved for the wired transmission from the receiving device 6 to the processing device 7 than for the wireless transmission, this is the only way of achieving uninterrupted transmission of the data packet.

However, since reception of the second data packet 26 is already complete at time 37, i.e. prior to the time 46 at which reception of the first data packet 28 is complete, the data packet 26 is transmitted first by the receiving device 6, and the data packet 24 is transmitted only after this transmission is complete. The timing of the transmitted data packets 24, 26 from the receiving device 6 to the processing device 7 is shown in line 34 in FIG. 2. By comparing lines 31 and 34, it is evident that the data packets 24, 26 are received by the processing device 7 in reverse transmission order, whereby re-ordering of the packet sequence in the processing device 7 would be necessary prior to further processing.

As explained above, this undesirable change in packet order can be avoided by delaying transmission of the second data packet 26 to the selected transmit buffer 17 until an enable condition evaluating the fill level of another transmit buffer, in the example transmit buffer 16, is fulfilled. An example of the evaluation of an enable condition is explained in more detail below with reference to FIG. 3.

Figure 3:
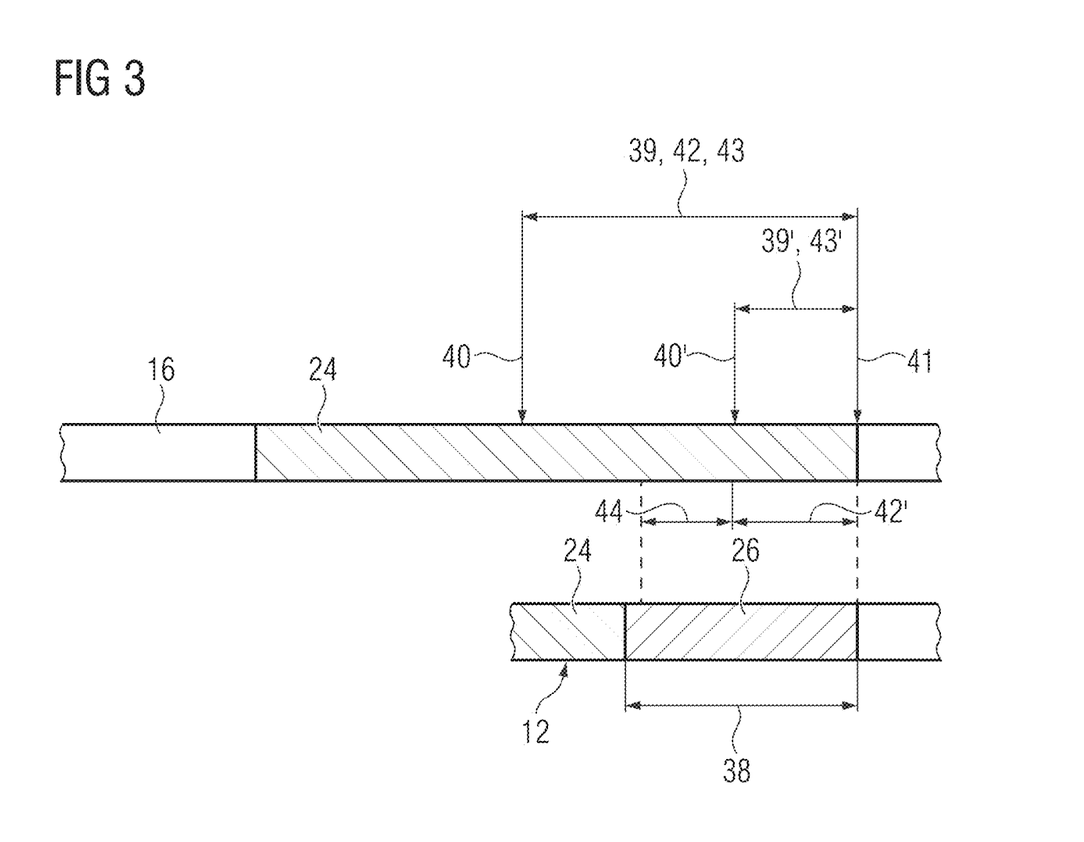
FIG. 3 illustrates the evaluation of the enable condition.

FIG. 3 schematically illustrates, on the one hand, the data packets 24, 26 stored in the receive buffer 12 and, on the other hand, the data packet 24 already transferred to the transmit buffer. Since the transfer of the data packet 24 to the transmit buffer 16 has already been completed, it would no longer need to be stored in the receive buffer 12 in the process state illustrated. However, FIFO buffers are often designed as circular buffers, wherein data that has already been read has already been swept by a read pointer, but remains in memory. The data is only overwritten when a write pointer reaches the data to be overwritten.

At time 25 when the second data packet is received, the first data packet has already been essentially fully transferred to the transmit buffer 16, so that a write pointer 41 of this buffer points to the end of the data packet 24. In addition, as can be seen in particular in line 32 in FIG. 2, since approximately half of the data of the data packet 24 has already been sent to the receiving device 6 and thus has already been read from the transmit buffer 16, the read pointer 40 of the transmit buffer 16 points approximately to the middle of the second data packet 24. The distance between the read and write pointers 40, 41 corresponds to the length 43 of the remaining partial data packet 42 of the data packet 24 that has not yet been sent to the receiving device 6 via the transmit interface 19 assigned to the transmit buffer 16. The length 43 can also be termed the fill level 39 of the transmit buffer 16.

As can be clearly seen in FIG. 3, the length 43 is greater than the length 38 of the data packet 26. However, this means that the data packet 26, if its data were transferred directly to the transmit buffer 17, would be expected to be transmitted completely to the receiving device 6 before the data packet 24, which would result in the change in packet order explained above. At time 25, the enable condition will not therefore be fulfilled.

FIG. 3 also shows the read pointer 40' at the position it occupies at time 62, i.e. after the end of the time interval 45, in line 35 of FIG. 2. Due to the continuous transmission and thus reading of data of the data packet 24, the read pointer has here shifted to the right toward the write pointer 41, so that the length 43' or rather the fill level 39' of the now remaining partial data packet 42' is smaller than the length 38 of the data packet 26.

Assuming that transmission of the data packets 24, 26 always results in the same transmission rates and latencies, the enable condition could always be fulfilled in this case and thus the transfer of the second data set 26 into the transmit buffer 17 could begin. However, in order to be able to reliably ensure a correct packet sequence even in cases where transmission times or rates vary, e.g. due to different possible transmission paths, possible interference affecting the wireless transmission path, etc., in the example shown the enable condition is only satisfied if the sum of the length 43, 43' of the remaining partial data packet 42, 42' and an offset value 44 is smaller than the length 38 of the data packet 26.

By using this enable condition, transmission of the second data packet 26 is delayed by the time interval 45, as can be seen from a comparison of lines 33, 35 in FIG. 2. As a result, reception of the data packet 26 by the receiving device 6 is only completed at a time later than the time 46 at which the first data packet 24 is fully received. This results in the data packets 24, 26 being transmitted in the correct order from the receiving device 6 to the processing device 7 when the enable condition 22 is used, as shown in line 36 in FIG. 2.

Figure 4:
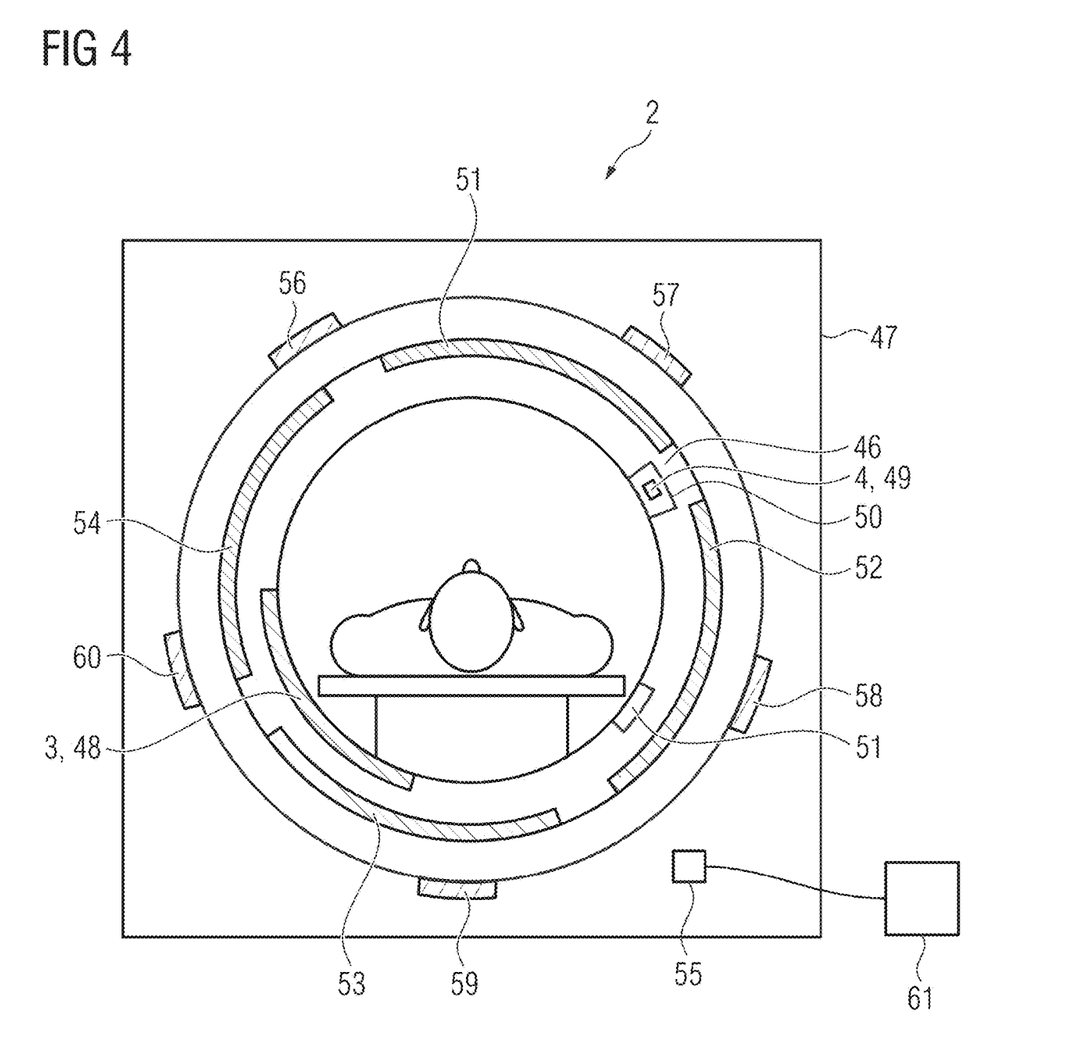
FIG. 4 shows another exemplary embodiment of a medical imaging device according to the present invention.

FIG. 4 schematically illustrates a specific example of a medical imaging device 2, namely a CT scanner, in which the teaching explained above is used for data transmission. The imaging device 2 comprises a base 47 and a framework 46 rotatably mounted with respect to the base 47, namely a gantry supporting an X-ray source 50 and, as sensor devices 48, 49 designed to supply data to a processing device 61 via the receiving device 55, an imaging X-ray detector and a voltage monitor of the X-ray tube 50. The measurement data of the sensor devices 48, 49 serving as data source 3, 4 is transmitted via a data transmission device 63 shown only schematically, which, apart from a different number of channels, essentially corresponds to the data transmission device 8 shown in FIG. 1. The large-area transmit antennas 51, 52, 53, 54 are each part of one of the transmit interfaces of the data transmission device 63 and thus, as already explained above, are fed by a respective transmit buffer.

The base-side receiving device 55 has five receive channels to which one of the receive antennas 56, 57, 58, 59, 60 is assigned in each case. Data streams received in parallel via these receive antennas are then serialized and transmitted to the processing device 61. As explained above, evaluation of an enable condition by the data transmission device 63 or rather its transfer device ensures that the correct packet sequence is reliably maintained despite this sectional use of parallel transmission paths.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in detail by exemplary embodiments, the present invention is not limited by the disclosed examples and other variations will be apparent to persons skilled in the art without departing from the scope of protection sought for the invention.

The invention claimed is:

1. A data transmission device for transmitting data packets, comprising:
   at least one receive interface configured to receive data packets from a respective data source;
   a respective receive buffer configured to buffer the data packets received via the respective receive interface;
   a transfer device configured to transfer the data packets from the respective receive buffer to a transmit buffer, the transmit buffer selected for the respective data packet from a plurality of existing transmit buffers; and
   a respective transmit interface configured to transmit the data packets stored in the respective transmit buffer to a receiving device, wherein the transfer device is configured to transfer the respective data packet from the respective receive buffer into the selected transmit buffer only when an enable condition exists, the enable condition being based on a fill level of one of the transmit buffers other than the selected transmit buffer and a length of the data packet to be transferred to the selected transmit buffer,
   wherein the fill level indicates a length of a remaining partial data packet or another data packet previously transferred into the one of the transmit buffers other than the selected transmit buffer, the partial data packet has not yet been transmitted via the transmit interface assigned to the one of the transmit buffers other than the selected transmit buffer, and
   wherein the enable condition exists if the length of the data packet to be transferred to the selected transmit buffer attains or exceeds the length of the partial data packet or a sum of the length of the partial data packet and a predetermined offset value.

2. The data transmission device as claimed in claim 1, wherein, for evaluating the enable condition, the transfer device is configured to consider, as the one of the transmit buffers other than the selected transmit buffer, the transmit buffer into which another data packet has been transferred which was received immediately prior to the data packet to be transferred into the selected transmit buffer.

3. The data transmission device as claimed in claim 2, wherein at least one of,
   the receive interface is connected or connectable by wire to the respective data source, or
   the respective transmit interface is configured for wireless transmission of the respective data packet to the receiving device.

4. The data transmission device as claimed in claim 1, wherein, for evaluating the enable condition, the transfer device is configured to consider, as the one of the transmit buffers other than the selected another transmit buffer, the transmit buffer into which another data packet has been transferred which was received via the same receive interface immediately before the data packet to be transferred to the selected transmit buffer.

5. The data transmission device as claimed in claim 4, wherein at least one of,
   the receive interface is connected or connectable by wire to the respective data source, or
   the respective transmit interface is configured for wireless transmission of the respective data packet to the receiving device.

6. The data transmission device as claimed in claim 1, wherein at least one of,
   the receive interface is connected or connectable by wire to the respective data source, or
   the respective transmit interface is configured for wireless transmission of the respective data packet to the receiving device.

7. The data transmission device as claimed in claim 1, wherein the data transmission device is configured to transmit measurement data of a medical imaging device as data packets.

8. A medical imaging device comprising the data transmission device as claimed in claim 1.

9. The medical imaging device as claimed in claim 8, further comprising:
   a sensor device, wherein the sensor device is configured to supply data packets to the data transmission device as the data source or via a processing device used as the data source.

10. The medical imaging device as claimed in claim 9, further comprising:
    a framework movably mounted with respect to a base, the framework incorporating the data source and the data transmission device, wherein the receiving device is fixed relative to the base.

11. The medical imaging device as claimed in claim 8, further comprising:
    a framework movably mounted with respect to a base, the framework incorporating the data source and the data transmission device, wherein the receiving device is fixed relative to the base.

12. The medical imaging device as claimed in claim 11, wherein at least one of,
    the medical imaging device is a CT scanner or comprises a CT scanner,
    a sensor device of the medical imaging device is an X-ray sensor or comprises an X-ray sensor, or
    the movably mounted framework is a rotatable gantry.

13. A method for transmitting data packets, the method comprising:
    receiving data packets from a respective data source;
    temporarily storing the received data packets in a receive buffer;
    transferring the data packets from the receive buffer into a transmit buffer selected for the respective data packet from a plurality of existing transmit buffers, wherein the respective data packet is only transferred from the respective receive buffer into the selected transmit buffer if an enable condition exists, the enable condition being based on a fill level of one of the transmit buffers other than the selected transmit buffer and a length of the data packet to be transferred to the selected transmit buffer, wherein the fill level indicates a length of a remaining partial data packet or another data packet previously transferred into the one of the transmit buffers other than the selected transmit buffer, the partial data packet having not yet been transmitted via a transmit interface assigned to the one of the transmit buffers other than the selected transmit buffer, and wherein the enable condition exists if the length of the data packet to be transferred to the selected transmit buffer attains or exceeds the length of the partial data packet or a sum of the length of the partial data packet and a predetermined offset value; and
    transmitting the data packets stored in the respective transmit buffer to a receiving device by a respective transmit interface assigned to the transmit buffer.

14. The method as claimed in claim 13, wherein at least one of,
    measurement data of a medical imaging device is transmitted as data packets, data packets are received from the respective data source via a wired connection, or the data packets stored in the respective transmit buffer are transmitted to the receiving device via a wireless connection by the respective transmit interface assigned to the transmit buffer.

15. A non-transitory computer readable medium, comprising instructions, during the execution of which data packets are transferred by a transfer device from a receive buffer to a transmit buffer selected for the respective data packet from a plurality of existing transmit buffers wherein transfer of the respective data packet from the respective receive buffer into the selected transmit buffer takes place only if an enable condition exists, the enable condition being based on a fill level of one of the transmit buffers other than the selected transmit buffer and a length of the data packet to be transferred to the selected transmit buffer, wherein the fill level indicates a length of a remaining partial data packet or another data packet previously transferred into the one of the transmit buffers other than the selected transmit buffer, the partial data packet having not yet been transmitted via a transmit interface assigned to the one of the transmit buffers other than the selected transmit buffer, and wherein the enable condition exists if the length of the data packet to be transferred to the selected transmit buffer attains or exceeds the length of the partial data packet or a sum of the length of the partial data packet and a predetermined offset value.

* * * * *